Figure 1:
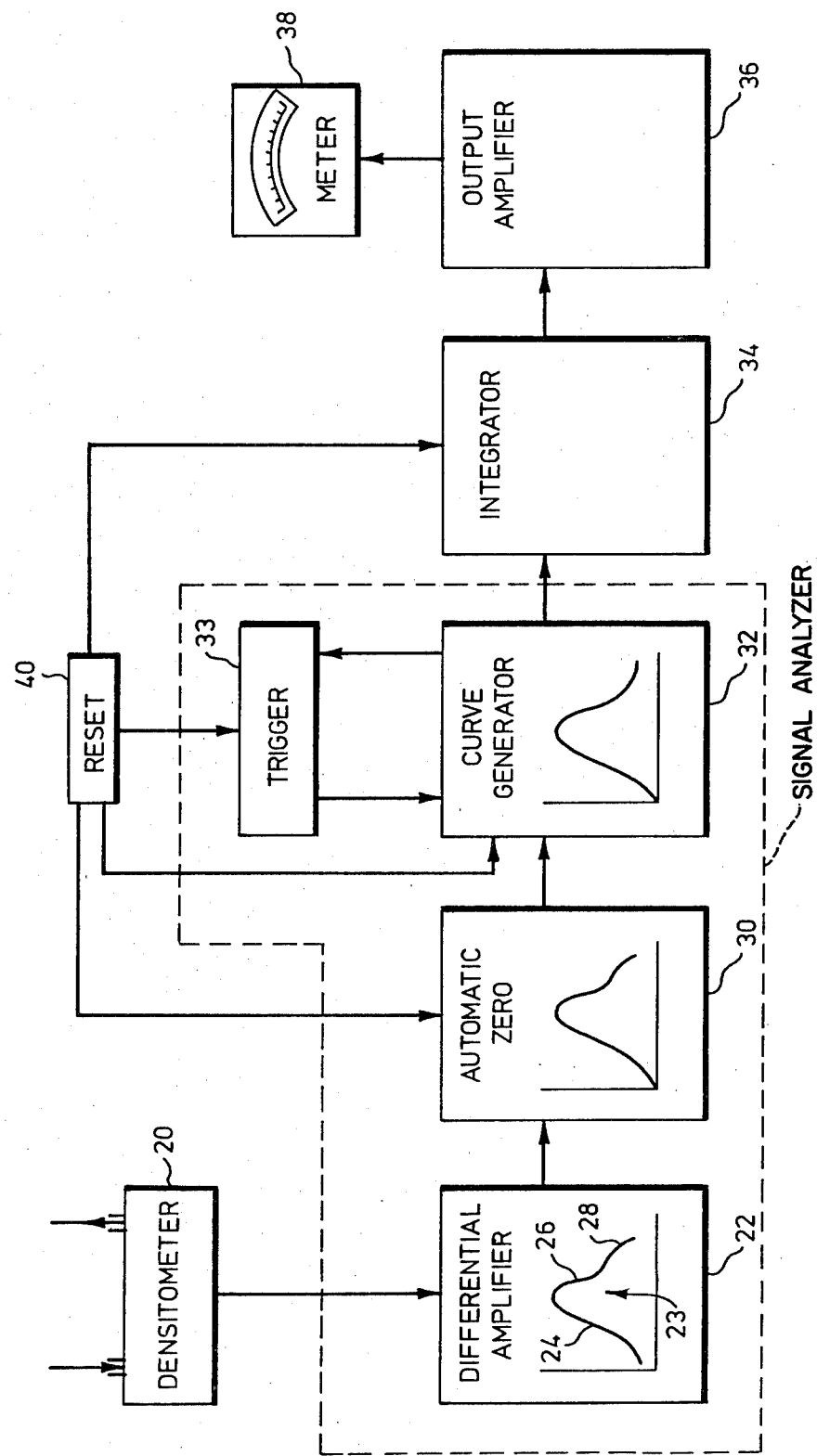

United States Patent [19]

Volgyesi

[11] 4,361,049
[45] Nov. 30, 1982

[54] APPARATUS FOR CALCULATING CARDIAC OUTPUT

[75] Inventor: George A. Volgyesi, Willowdale, Canada

[73] Assignee: The Hospital for Sick Children, Toronto, Canada

[21] Appl. No.: 179,341

[22] Filed: Aug. 18, 1980

[51] Int. Cl.³ .................... G01P 5/18; A61B 5/02; H01J 40/14
[52] U.S. Cl. ...................... 73/861.05; 73/861.07; 128/654; 128/713; 250/211 K; 250/214 L; 307/492
[58] Field of Search .......... 73/861.05, 861.06, 861.07; 128/654, 692, 713; 250/211 K, 214 L; 307/492, 517

[56] References Cited

U.S. PATENT DOCUMENTS

| | | | |
|---|---|---|---|
| 3,450,939 | 6/1969 | Misencik | 307/311 |
| 3,646,439 | 2/1972 | Broski | 307/311 X |
| 3,651,318 | 3/1972 | Czekajewski | 128/654 X |
| 3,735,288 | 5/1973 | Strauss | 307/311 X |
| 3,859,602 | 1/1975 | Janssen et al. | 128/713 X |
| 3,987,788 | 10/1976 | Emil | 128/713 |

Primary Examiner—Anthony V. Ciarlante
Assistant Examiner—David V. Carlson
Attorney, Agent, or Firm—Rogers, Bereskin & Parr

[57] ABSTRACT

The invention provides apparatus for measuring the rate of flow of liquid being circulated in a closed loop system by a pump using a bolus of indicator injected suddenly into the system upstream of the pump and a sampling station downstream of the pump. The apparatus includes signal means for location at the sampling station to provide an electrical signal proportional to the indicator passing this station. The electrical signal has an increasing portion, a decaying exponential portion, and a distorted portion caused by recirculation of the indicator in the system. A signal analyzer is coupled to the signal means to receive the electrical signal and includes a wave generator sensitive to the exponential portion and including extrapolation means for providing a portion of the exponential curve lost by interference by recirculation. The signal analyzer provides an output signal corresponding to the increasing portion, the exponential portion, and the portion provided by the extrapolation means. The apparatus also includes signal interruption means operable to discontinue the electrical signal before the curve reaches the distorted portion to avoid interference of this portion in the extrapolation of the exponential portion. Also, integrator means is coupled to the signal analyzer to receive the output signal and to provide a reading of the rate of flow of the liquid.

3 Claims, 2 Drawing Figures

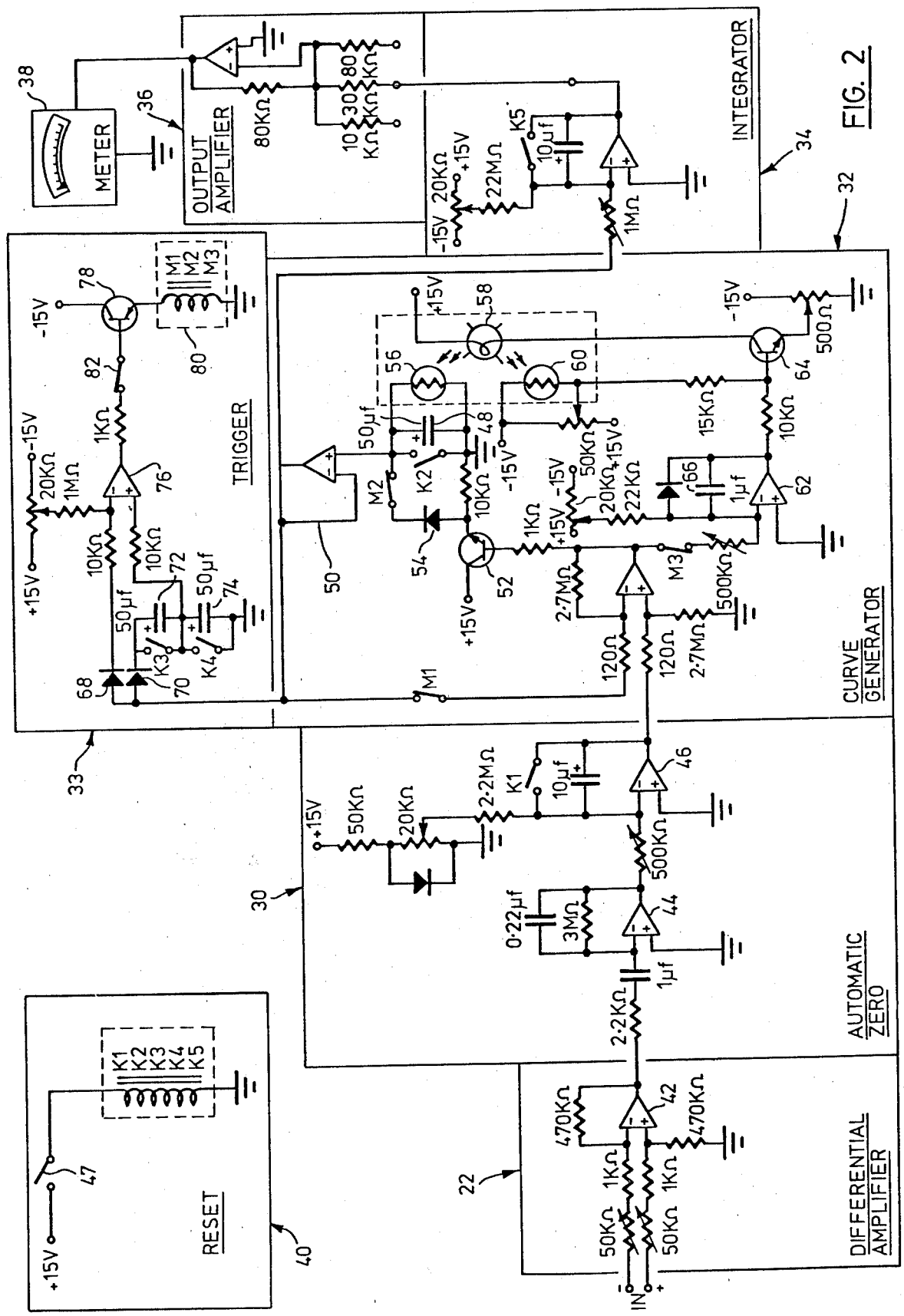

APPARATUS FOR CALCULATING CARDIAC OUTPUT

This invention relates to a method and apparatus for determining flow rate in a closed liquid system such as the blood circulatory system.

The invention will be described with particular reference to blood circulation which is normally termed "cardiac output". However it will be apparent by analogy that the invention can be used to determine the rate of flow in other closed circulation systems.

Cardiac output is defined as the rate of flow of blood (measured normally in liters per minute) and is a function of heart condition. For proper detection and treatment of many cardiac disorders it is necessary to ascertain as accurately as possible the rate at which blood is being pumped through the circulatory system. There are many techniques in use but most rely on the use of a dye or other indicator which is injected suddenly upstream of the heart and analyzed downstream of the heart. In the case of a dye the density of dye in the blood increases initially to a maximum and then decays exponentially. The curve produced establishes an area under the curve indicative of the volume of blood pumped by the heart and the time taken for this blood to pass the point where analysis is being made. Of course before the density of the dye can taper off exponentially to substantially zero, recirculation of the dye will produce a second peak in the density curve introducing a distortion to the decaying exponential portion of the curve. This distortion cannot be tolerated if an accurate reading of cardiac output is to be established and various methods have been proposed to compensate for the distortion.

The original method is known as the Stewart-Hamilton method and tends to be a rather laborious manual operation. In this method the density of the dye is plotted against time using a semi-logarithmic graph paper. As the density of the dye begins to diminish, a curve is established which can then be used to extrapolate the remainder of the exponential curve so that the distortion caused by the second pulse can be eliminated. Theoretically this method is the most accurate but it is impractical when results are required quickly.

A second approach is to use a geometrical approximation. One example of this approach is shown in U.S. Pat. No. 3,618,591 in which triangular areas are made to approximate the area under the exponential curve by using the maximum height of the curve and points at 50 percent of this height. Methods of this type also suffer from significant inaccuracy.

A third approach is shown in U.S. Pat. No. 3,651,318. In this patent two points are detected on the exponential decay from the density peak and used to extrapolate the integral of the remainder of the wave form. A computer is used to give a resulting flow rate and although this method appears to have advantages over some earlier methods, it nevertheless suffers from obvious inaccuracy if one of the detection points happens to be an aberration from the main curve. It is suggested that such inaccuracy would be intolerable when treating patients having radical disorders of the heart.

It is one of the aspects of the present invention to provide apparatus for measuring the rate of flow of liquid being circulated in a closed loop system by a pump using a bolus of indicator injected suddenly into the system upstream of the pump and a sampling station downstream of the pump. The apparatus includes signal means for location at the sampling station to provide an electrical signal proportional to the indicator passing this station. The electrical signal has an increasing portion, a decaying exponential portion, and a distorted portion caused by recirculation of the indicator in the system. A signal analyzer is coupled to the signal means to receive the electrical signal and includes a wave generator sensitive to the exponential portion and including extrapolation means for providing a portion of the exponential curve lost by interference by recirculation. The signal analyzer provides an output signal corresponding to the increasing portion, the exponential portion, and the portion provided by the extrapolation means. The apparatus also includes signal interruption means operable to discontinue the electrical signal before the curve reaches the distorted portion to avoid interference of this portion in the extrapolation of the exponential portion. Also, integrator means is coupled to the signal analyzer to receive the output signal and to provide a reading of the rate of flow of the liquid.

The invention will be better understood with reference to the drawings, in which:

FIG. 1 is a diagrammatic representation of a preferred embodiment of the invention; and FIG. 2 is a circuit diagram further illustrating the embodiment.

The preferred embodiment of the apparatus is shown in the drawings and is intended for use specifically in evaluating the performance of a human subject's heart. A bolus of conventional indicator dye is injected into a vein upstream of the heart and monitored at a sampling station located downstream of the heart. The blood is monitored using a densitometer 20 as shown in FIG. 1. This densitometer produces an analog signal proportional to the density of dye in the blood and this signal is fed to a differential amplifier 22. A typical curve illustrated at 23 consists of an increasing first portion 24 followed by a decaying exponential portion 26 and by a distorted portion 28 which results from the recirculation of the dye affecting the decay which would normally be exponential. In order to obtain the true area under the curve 23 it is necessary to extrapolate the portion 26 and to ignore the distorted portion 28.

After amplification by the differential amplifier 22, an analog signal is fed to an automatic zero 30 which effectively sets the curve 23 on the time axis to avoid integration inaccuracies caused by incorrect location of the curve relative to this axis. After this adjustment the analog signal is fed to a curve generator 32 which (as will be described) is capable of locking onto the portion 26 of the curve and extrapolating this portion to provide a true exponential decay. In effect the result is to provide a curve which would have resulted if recirculation of the dye could have been ignored.

In order to provide this extrapolation it is necessary to disengage the curve generator from the automatic zero 30 before the distorted portion 28 of the curve is fed to the curve generator. This is achieved using a trigger 33 which will also be described more fully with reference to FIG. 2.

Having achieved a corrected curve the analog signal from the curve generator 32 is fed to an integrator 34 and the resulting signal is amplified using an output amplifier 36 and fed to a meter 38.

It will be evident that other pieces of equipment can be added to the circuit. For instance a trace of the actual curve obtained from the curve generator could be obtained independently of the remainder of the apparatus shown in FIG. 1.

FIG. 1 also illustrates a reset 40 connected to the automatic zero 30, the trigger 33, the curve generator 32, and the integrator 34 to discharge potentials remaining in these parts of the apparatus preparatory to analysing another cardiac output curve.

Reference is next made to FIG. 2 to describe the apparatus in more detail. The differential amplifier 22 permits the standardization of the relationship between indicator concentration and voltage so that any densitometer can be used. As a result the differential amplifier must accept either single ended or differential inputs and provide gain which is adjustable between wide limits. For these reasons a Fairchild $\mu$A741 operational amplifier 42 is used in a symmetrical differential input configuration as seen in FIG. 2.

The automatic zero 30 receives an analog signal from the differential amplifier. The automatic zero circuit then differentiates and integrates the signal input to adjust the baseline to ground potential. This is done by closing a switch 47 momentarily in reset 40 to thereby close switch K1. This adjusts the output signal to zero before the curve signal is received from the differential amplifier. The circuit used is shown in FIG. 2 and the operational amplifiers 44, 46 are similar to the amplifier 42 used in the differential amplifier 22.

The curve generator 32 will now be described. Initially an increasing signal from the automatic zero 30 is compared with a charge on a capacitor 48 by way of a follower 50. The difference between the signals is amplified and activates a transistor 52 thereby charging the capacitor 48 by way of a diode 54. As the signal from the automatic zero continues to increase there will be a continued difference between this signal and feedback from the capacitor 48 so that there will be a continuing increase in the charge on the capacitor. The increase is sufficiently rapid to offset any decay which may occur through a high light-sensitive resistance 56 sealed within a light box together with a bulb 58 and a further light-sensitive resistance 60. During this increasing signal from the automatic zero an integrator 62 will be inactive so that only that portion of the circuit including the capacitor 48 will be energized and the bulb 58 will be inactive.

When the signal from the automatic zero 30 reaches a maximum the capacitance charge will match the input and subsequently as the input signal begins to decrease the transistor 52 will be inactive leaving the capacitor 48 energized. However the decreasing signal will then cause an output from the integrator 62 thereby energizing transistor 64 and drawing current through the light bulb 58. This current causes the light bulb to glow and thereby increases the conductance of the light-sensitive resistance 58 so that the capacitor 48 can discharge controlled by the resistance 56. This reduction in charge will tend to follow the reduction in signal from the automatic zero so that a position will be reached where the decay rate of the capacitor 48 linked with the resistance 56 matches the decay rate of the curve from the automatic zero. The resistor 60 is used as a damper to minimize sudden changes in light intensity from the bulb 58.

Once the decay rate has been established it is necessary to discontinue the signal from the automatic zero so that the distorted signal resulting from recirculation is not fed to the curve generator. This is achieved using the trigger 33. However it will be appreciated that the light 58 must continue to glow at the precise intensity established previously to ensure that the capacitor 48 continues to discharge under the steady conditions established by locking into the exponential portion of the signal from the automatic zero. This is done by the integrator 62 which holds its output steady when its input is disconnected to maintain the transistor 64 active thereby causing the light bulb 58 to remain energized.

The trigger 33 is sensitive to the charge on the capacitor 48. During an increasing signal the same charge is applied through similar diodes 68, 70 respectively to a main part of the circuit and to a pair of similar capacitors 72, 74 arranged in series. As a result of this arrangement half of the voltage in the main circuit of the trigger beyond the diode 70 is found between the capacitors 72, 74. An operation amplifier 76 then compares this half voltage with the reducing voltage as the charge on capacitor 48 diminishes. The arrangement is such that when this reducing voltage matches the half voltage, the polarity of the output from the amplifier 76 is reversed so that a transistor 78 is no longer energized and a relay 80 is de-energized to allow the normally-open switches M1, M2, and M3 to open. These switches effectively isolate the curve generator from the automatic zero so that the output from the curve generator then depends upon the exponential decay of the capacitor 48. This signal is then passed to the integrator 34.

The integrator 34 evaluates electronically the area under the curve generated by the curve generator 32. The voltage output from the integrator is inversely proportional to the cardiac output. Subsequently the output is amplified in the output amplifier and fed to the meter 38.

After a reading has been obtained the reset switch 47 is used to close the normally-open contacts K1, K2, K3, K4 and K5 momentarily thereby discharging capacitors in the automatic zero, curve generator, trigger and integrator. The equipment is then ready to analyze another curve.

In some instances it may be preferable to activate the trigger manually before the signal from the automatic zero has decayed to half of the maximum signal.

This can be done using a manual switch 82 adjacent the transistor 78 of the trigger. Once the switch 82 is opened then the switches M1, M2, M3 open having the same effect as the trigger when the decaying voltage reached half the maximum voltage.

It will now be evident that the apparatus described locks onto the decaying signal from the automatic zero and extrapolates the decaying pulse signal exponentially in accordance with a constant set up by the capacitor 48 in combination with the light-sensitive resistance 56. This resistance together with the resistance 60 are photo-conducting cells sold by Clairex and designated number 703 CL. They are used in combination with a lamp having a resistance of 40 ohms and rated at 28 volts.

I claim:

1. Apparatus for measuring the flow rate of liquid being circulated in a closed system by a pump using a bolus of indicator injected suddenly into the system upstream of the pump and a sampling station downstream of the pump, the apparatus comprising:

signal means for location at the sampling station and adapted to provide an electrical signal proportional to the concentration of the indicator passing said station, the electrical signal having an increasing portion followed by a decaying exponential portion and a distorted portion caused by recirculation of the indicator;

a signal analyzer coupled to said signal means to receive said electrical signal and adapted to provide a continuous output during the whole of said electrical signal corresponding to said increasing portion and said decaying exponential portion and including an extrapolated exponential portion replacing said distorted portion of the signal, said signal analyzer including: means to automatically zero said signal on a time base; a curve generator for receiving said signal from the zeroing means, said curve generator including a capacitor which is charged by said signal while the signal is increasing, said curve generator being adapted to continuously compare the charge on said capacitor with said signal and to permit said capacitor to discharge exponentionally after said signal has reached a peak, at a rate matched to the decay rate of the electrical signal; said discharge rate continuously following said signal exponential decay rate and trigger means coupled to said curve generator and responsive to the charge on said capacitor, said trigger means being adapted to isolate the curve generator from said electrical signal when said charge on said capacitor has fallen to a predetermined level corresponding to a time during said exponential portion of said electrical signal and in advance of said distorted portion, whereby said signal analyzer output thereafter decays exponentially without interference from said distorted portion of the electrical signal; and, integrator means receiving said continuous signal analyzer output and adapted to integrate said output and provide a reading of the flow rate of the liquid.

2. Apparatus as claimed in claim 1 in which said capacitor is arranged in parallel with a light-sensitive resistance and a light source positioned to illuminate the light-sensitive resistance and responsive to changes in the difference between the charge on the capacitor and signal values in the exponential portion of said electrical signal to thereby provide feedback to adjust the conductance of the light-sensitive resistance so that the said difference is eliminated continuously prior to activation of said trigger means.

3. Apparatus as claimed in claim 1 or 2 in which the signal means is a densitometer.

* * * * *